United States Patent
Chiem

(10) Patent No.: US 12,214,116 B2
(45) Date of Patent: *Feb. 4, 2025

(54) METHODS AND SYSTEMS FOR PROVIDING CONTROL STABILITY IN A VACUUM GENERATION SYSTEM USING CASCADE PROPORTIONAL-INTEGRAL-DERIVATIVE (PID) CONTROLLER

(71) Applicant: Alcon Inc., Fribourg (CH)

(72) Inventor: Brian T. Chiem, San Gabriel, CA (US)

(73) Assignee: Alcon Inc., Fribourg (CH)

( * ) Notice: Subject to any disclaimer, the term of this patent is extended or adjusted under 35 U.S.C. 154(b) by 646 days.

This patent is subject to a terminal disclaimer.

(21) Appl. No.: 17/460,630

(22) Filed: Aug. 30, 2021

(65) Prior Publication Data

US 2022/0080098 A1  Mar. 17, 2022

Related U.S. Application Data

(60) Provisional application No. 63/077,753, filed on Sep. 14, 2020.

(51) Int. Cl.
*A61M 1/00* (2006.01)
*A61F 9/007* (2006.01)
*G05D 16/20* (2006.01)

(52) U.S. Cl.
CPC .............. *A61M 1/74* (2021.05); *A61M 1/743* (2021.05); *G05D 16/2066* (2013.01);
(Continued)

(58) Field of Classification Search
CPC .... A61M 1/74; A61M 1/743; A61M 2205/50; A61M 2205/3331; A61M 2210/0612;
(Continued)

(56) References Cited

U.S. PATENT DOCUMENTS

| 4,838,281 A | 6/1989 | Rogers et al. |
| 4,850,377 A | 7/1989 | Parker et al. |

(Continued)

FOREIGN PATENT DOCUMENTS

| EP | 0770940 A1 | 5/1997 | |
| EP | 3627244 A1 | 3/2020 | |
| WO | WO-2020068823 A1 * | 4/2020 | .............. A61M 1/72 |

OTHER PUBLICATIONS

Brian T. Chiem, "Methods and Systems for Providing Control Stability in a Vacuum Generation System Using an Override Proportional-Integral-Derivative (PID) Controller," U.S. Appl. No. 17/376,330, filed Jul. 15, 2021, pp. 1-28.

(Continued)

*Primary Examiner* — Chad G Erdman
(74) *Attorney, Agent, or Firm* — Patterson + Sheridan, LLP

(57) ABSTRACT

Certain embodiments provide a vacuum generation system with a cascade PID controller, a proportional valve, and a vacuum generator. The cascade PID controller allows the vacuum generation system to control the operating range of supply air pressure that is provided to the vacuum generator. By controlling the operating range of the supply air pressure, the vacuum generation system is able to avoid entering the decreasing or non-monotonic region of the vacuum generator.

15 Claims, 9 Drawing Sheets

(52) U.S. Cl.
CPC ....... *A61F 9/00736* (2013.01); *A61F 9/00745* (2013.01); *A61M 2205/50* (2013.01)

(58) Field of Classification Search
CPC .... A61M 1/73; A61M 1/804; G05D 16/2066; A61F 9/00736; A61F 9/00745
See application file for complete search history.

(56) References Cited

U.S. PATENT DOCUMENTS

| | | | |
|---|---|---|---|
| 5,354,268 A | | 10/1994 | Peterson |
| 5,674,194 A | * | 10/1997 | Jung ..................... A61M 1/743 604/118 |
| 7,524,299 B2 | | 4/2009 | Hopkins |
| 8,162,000 B2 | | 4/2012 | Turner |
| 10,795,323 B2 | | 10/2020 | Skertic |
| 2007/0005029 A1 | | 1/2007 | Hopkins |
| 2009/0124962 A1 | | 5/2009 | Hopkins et al. |
| 2015/0297311 A1 | * | 10/2015 | Tesar .................. G02B 21/0012 600/109 |
| 2018/0207032 A1 | | 7/2018 | Charles et al. |
| 2019/0143008 A1 | * | 5/2019 | Brundage ............... A61M 1/74 604/30 |
| 2021/0213183 A1 | | 7/2021 | Zhou |

OTHER PUBLICATIONS

Åström, K. and T. Hägglund, PID Controllers: Theory, Design, and Tuning. ISA: The Instrumentation, Systems, and Automation Society; 2nd Edition, 1995, pp. 274-277 and 292-294.

Chiem, Brian T., "Methods and Systems for Providing Control Stability in a Vacuum Generation System Using Cascade Proportional-Integral-Derivative (PID) Controller," U.S. Appl. No. 17/460,630, filed Aug. 30, 2021, pp. 1-25.

* cited by examiner

METHODS AND SYSTEMS FOR PROVIDING CONTROL STABILITY IN A VACUUM GENERATION SYSTEM USING CASCADE PROPORTIONAL-INTEGRAL-DERIVATIVE (PID) CONTROLLER

PRIORITY CLAIM

This application claims the benefit of priority of U.S. Provisional Patent Application Ser. No. 63/077,753 titled "METHODS AND SYSTEMS FOR PROVIDING CONTROL STABILITY IN A VACUUM GENERATION SYSTEM USING CASCADE PROPORTIONAL-INTEGRAL-DERIVATIVE (PID) CONTROLLER," filed on Sep. 14, 2020, whose inventor is Brian T. Chiem, which is hereby incorporated by reference in its entirety as though fully and completely set forth herein.

TECHNICAL FIELD

The present disclosure relates generally to methods and systems for providing control stability in a vacuum generation system using a cascade proportional-integral-derivative (PID) controller.

BACKGROUND

During small incision surgery, and particularly during ophthalmic surgery, small probes are inserted into the operative site to cut, remove, or otherwise manipulate tissue. During these surgical procedures, fluid and tissue may be aspirated from the surgical site.

Examples of ophthalmic surgeries during which fluid and tissue are aspirated include vitreo-retinal procedures. Vitreo-retinal procedures may include a variety of surgical procedures performed to restore, preserve, and enhance vision. Vitreo-retinal procedures may be appropriate to treat many serious conditions of the back of the eye. Vitreo-retinal procedures may treat conditions such as age-related macular degeneration (AMD), diabetic retinopathy and diabetic vitreous hemorrhage, macular hole, retinal detachment, epiretinal membrane, CMV retinitis, and many other ophthalmic conditions. In order to treat certain conditions in the back of the eye, a surgeon may first perform vitrectomy, as part of the vitreo-retinal procedure that is being performed. Vitrectomy refers to a surgical removal of the vitreous, which is a normally clear, gel-like substance that fills the center of the eye. The vitreous may make up approximately two-thirds of the eye's volume, giving it form and shape before birth.

Removal of vitreous can involve a vitrector (also referred to as the "cutter" or "vitreous cutter"). In some examples, the vitrector may be powered by a pneumatic vitrectomy machine (e.g., surgical console) including one or more pneumatic valves (also referred to as drive valves). In such examples, the vitrector may work like a tiny guillotine, with an oscillating microscopic cutter to remove the vitreous gel in a controlled fashion. In some other examples, the vitrector may cut the vitreous using laser light or some other technology such as ultrasound. In addition to cutting the vitreous, the cutter may also be configured to aspirate the surgically cut vitreous. Aspiration may be provided by a vacuum generator (e.g., venturi vacuum) that is coupled to the cutter through a tube that provides an aspiration channel.

Other examples of ophthalmic surgeries during which fluid and tissue are aspirated include phacoemulsification, which refers to a cataract operation in which a diseased lens is emulsified and aspirated out of the lens capsule. In some examples, the phacoemulsification probe may break up the lens by ultrasound (or other technologies, such as laser light, etc.). For aspirating the broken up lens, the phacoemulsification probe may be powered by a vacuum generator (e.g., venturi vacuum) that is coupled to the phacoemulsification probe through a tube that provides an aspiration channel.

Certain existing vacuum generators, such as certain existing venturi vacuum generators, operate using compressed air to flow through orifices that generate vacuum pressure. However, a common property of these vacuum generators is that beyond a certain amount of supply pressure, the vacuum generator becomes less efficient and generates less vacuum pressure as supply pressure increases. For example, vacuum pressure increases as the supply air pressure increases in the range of 0-60 psig (pounds per square inch gauge). However, vacuum pressure begins to decrease as the supply air pressure increases in the range of 60-87 psig. More specifically, when the supply air pressure reaches around 60 psig and higher, vacuum pressure starts decreasing, thereby causing a standard PID controller, which is used to regulate the supply air pressure, to drive to instability. In such an example, when the supply air pressure is in the range of 0-60 psig, the vacuum generator may be referred to as being operating in a monotonic region. On the other hand, when the supply air pressure is above 60 psig, the vacuum generator may be referred to as being operating in a non-monotonic or decreasing region.

BRIEF SUMMARY

The present disclosure relates generally to methods and systems for providing control stability in a vacuum generation system using a cascade proportional-integral-derivative (PID) controller.

Certain embodiments provide a method of controlling vacuum pressure in a vacuum generation system. The method comprises receiving a vacuum pressure sensor reading from a vacuum pressure sensor. The method further comprises calculating a first error between the vacuum pressure sensor reading and a vacuum pressure set point. The method further comprises calculating a supply air pressure set point based on the first error. The method further comprises receiving a supply air pressure sensor reading from a supply air pressure sensor. The method further comprises calculating a second error between the supply air pressure sensor reading and the supply air pressure set point. The method further comprises calculating a voltage level for controlling a proportional valve based on the second error. The method further comprises providing the voltage level to the proportional valve. The method further comprises causing, using the proportional valve, supply air pressure to be provided to a vacuum generator based on the voltage level. The method further comprises providing, using the vacuum generator, vacuum pressure based on the supply air pressure to a surgical tool.

Certain embodiments provide a vacuum generation system. The vacuum generation system comprises a first proportional-integral-derivative (PID) controller, configured to receive a first error between a vacuum pressure sensor reading associated with a vacuum generator and a vacuum pressure set point, and calculate a supply air pressure set point based on the first error. The vacuum generation system further comprises a second PID controller, configured to receive a second error between a supply air pressure sensor reading and the supply air pressure set point, and calculate a voltage level based on the second error. The vacuum generation system further comprises the proportional valve configured to receive the voltage level and cause supply air pressure to be provided to a vacuum generator based on the voltage level. The vacuum generation system further comprises the vacuum generator configured to provide vacuum pressure based on the supply air pressure to a surgical tool.

Certain embodiments provide a vacuum generation system comprising a memory comprising executable instructions and a processor in data communication with memory and configured to execute the instructions, which configured the processor to: receive a first error between a vacuum pressure sensor reading associated with a vacuum generator and a vacuum pressure set point; calculate a supply air pressure set point based on the first error, receive a second error between a supply air pressure sensor reading and the supply air pressure set point, calculate a voltage level based on the second error, and cause the voltage level to be provided to the proportional valve. The vacuum generation system further comprises the proportional valve, configured to cause supply air pressure to be provided to a vacuum generator based on the voltage level. The vacuum generation system further comprising the vacuum generator configured to provide vacuum pressure based on the supply air pressure to a surgical tool.

The following description and the related drawings set forth in detail certain illustrative features of one or more embodiments.

BRIEF DESCRIPTION OF THE DRAWINGS

The appended drawings depict only examples of certain embodiments of the present disclosure and are therefore not to be considered as limiting the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with various other embodiments discussed herein. In similar fashion, while exemplary embodiments may be discussed below as device, instrument, or method embodiments it should be understood that such exemplary embodiments can be implemented in various devices, instruments, and methods.

Figure 1:
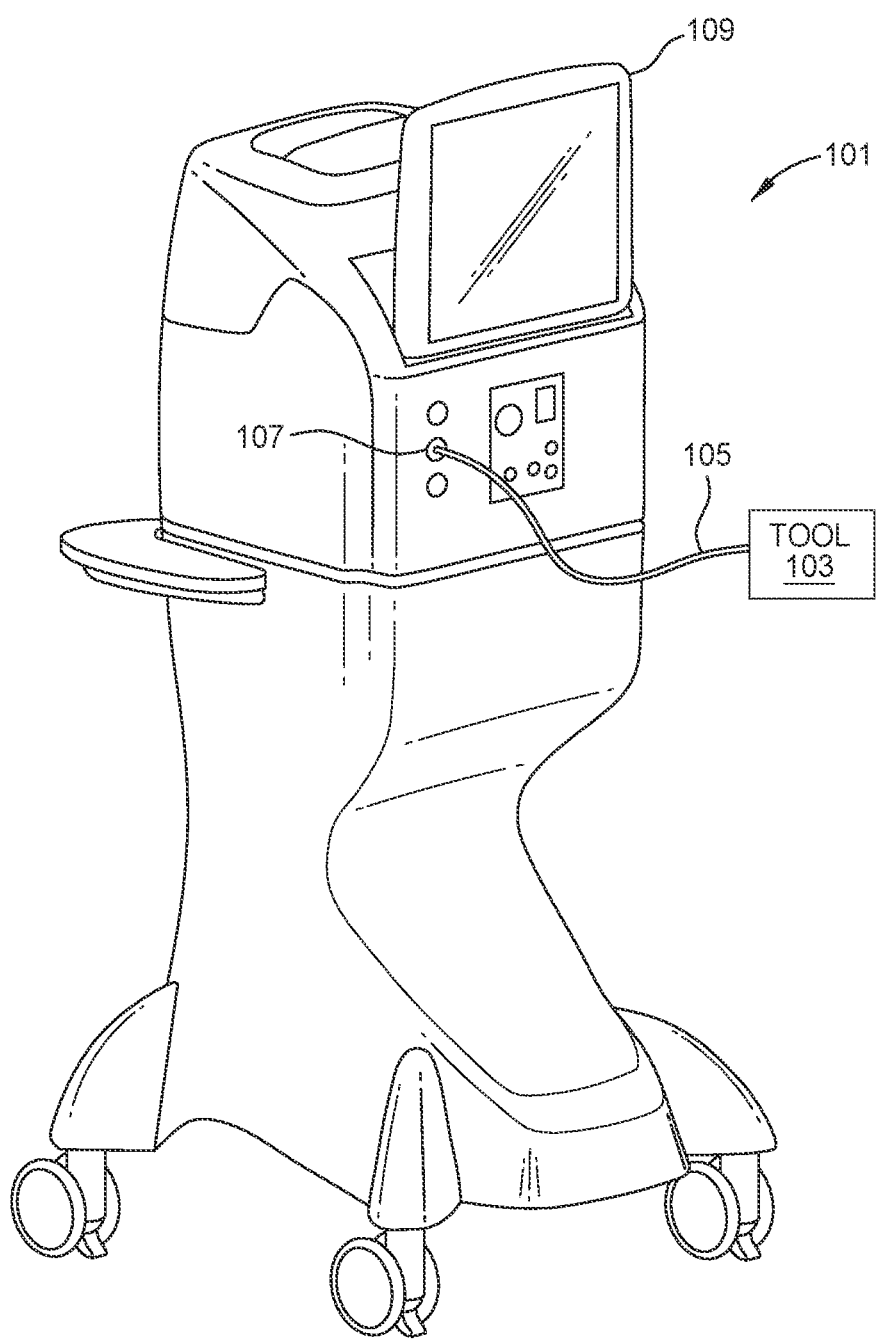
FIG. 1 illustrates an example surgical console, in accordance with certain embodiments.

FIG. 1 illustrates an example of a surgical console 101, according to certain embodiments. Surgical console 101 may be configured to drive one or more tools 103, which may include vitrectors, phacoemulsification probes, and other tools with aspiration functionality. In operation, surgical console 101 may function to assist a surgeon in performing various ophthalmic surgical procedures, such as vitrectomy, phacoemulsification, and similar procedures. In embodiments where tool 103 is a vitrector, surgical console 101 includes one or more modules or components to power the vitrector for the purpose of cutting the vitreous. For example, in certain embodiments, surgical console 101 may include a pneumatic module that uses compressed gas, such as nitrogen, to power the vitrector. In certain other embodiments, surgical console 101 may include a laser source for generating laser light that is used by the vitrector to cut the vitreous. In embodiments where tool 103 is a phacoemulsification probe, surgical console 101 includes one or more modules or components to power the phacoemulsification probe to emulsify the lens during cataract surgery.

The surgical console 101 may include a display 109 for displaying information to a user (the display may also incorporate a touchscreen for receiving user input). The surgical console 101 may also include a vacuum generator that is coupled to a port 107. Tool 103 is operatively coupled to the vacuum generator through a line 105 that connects to port 107. The vacuum generator creates vacuum at the tip of tool 103, which causes the surgically cut or emulsified material or tissue to be vacuumed into tool 103 and transported along line 105 to surgical console 101. Note that line 105 may be representative of a number of tubes that may couple tool 103 with surgical console 101. For example, line 105 may be representative of a pneumatic line or an optical fiber cable for powering tool 103 for cutting purposes as well as an aspiration or vacuum line for transporting the aspirated material back to surgical console 101.

Figure 2:
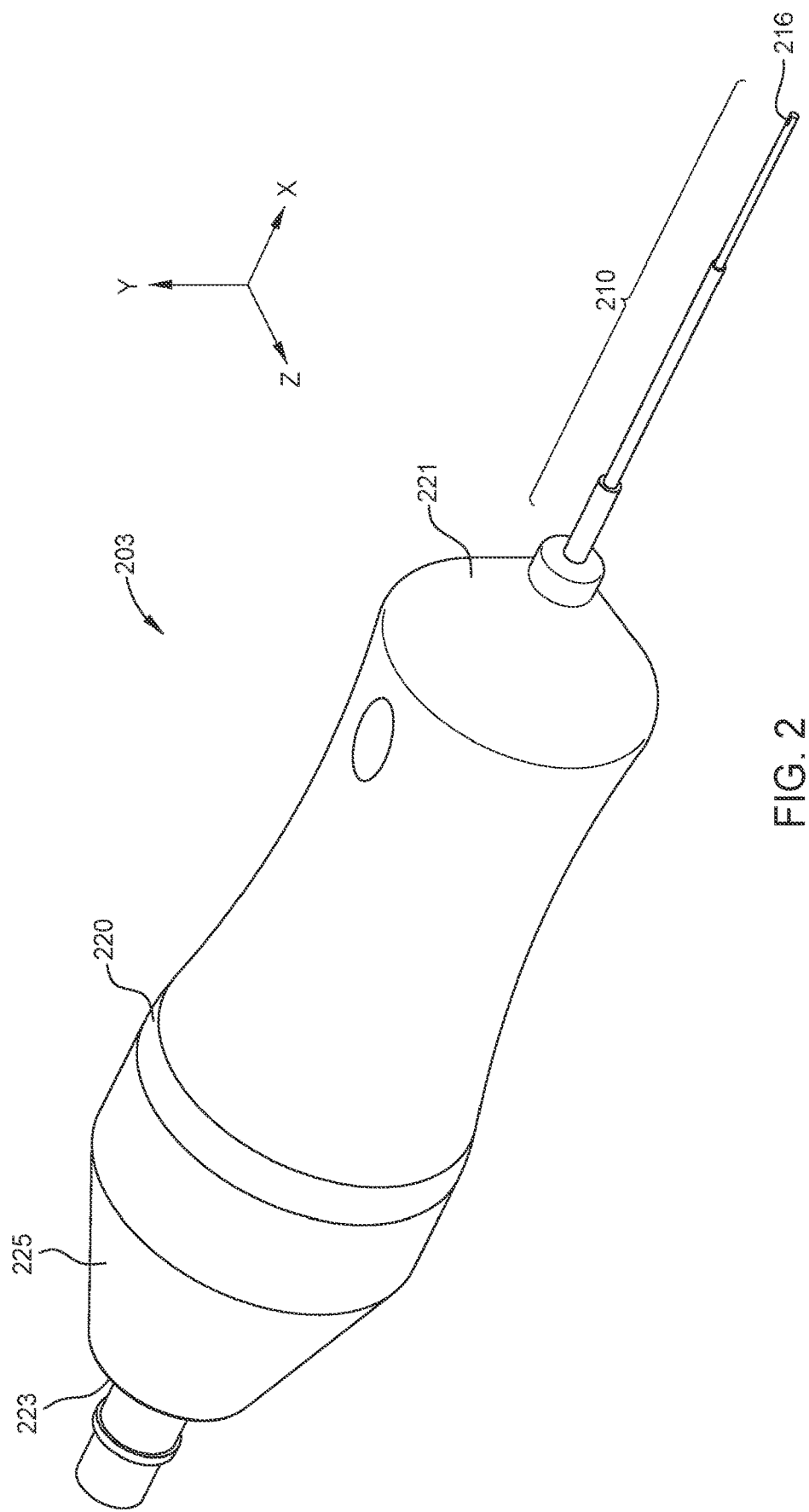
FIG. 2 illustrates an example vitrectomy probe, in accordance with certain embodiments.
Figure 3:
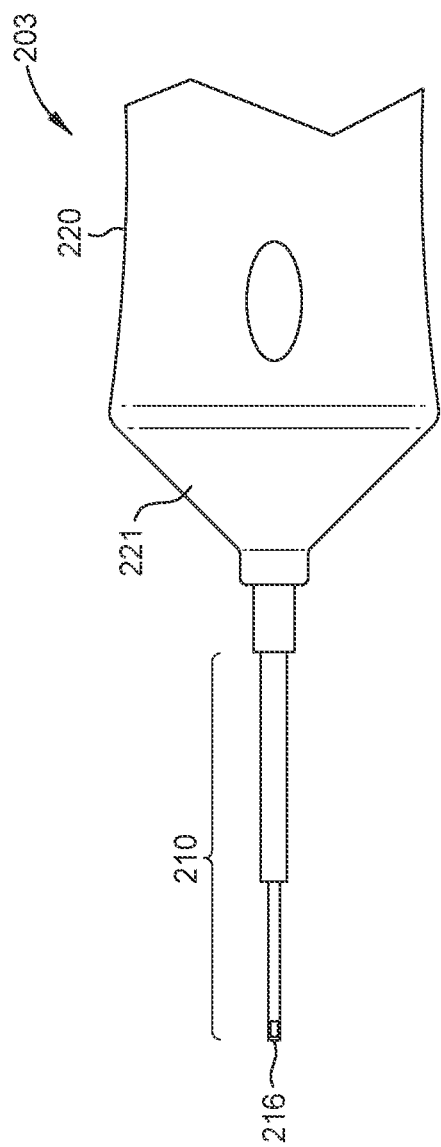
FIG. 3 illustrates a side vide of the vitrectomy probe of FIG. 2, in accordance with certain embodiments.

FIGS. 2 and 3 illustrate a perspective view and a side view of an exemplary vitrector 203, respectively, according to certain embodiments described herein. FIGS. 2 and 3, therefore, are described together for clarity. Vitrector 203 is an example of tool 103. As depicted in FIGS. 2-3, vitrector 203 comprises a probe 210 and a base unit 220. Probe 210 is partially and longitudinally disposed through a distal end 221 of base unit 220 and may be directly or indirectly attached thereto within an interior chamber of base unit 220. Probe 210 may be inserted into an eye for performing vitrectomy. Note that, as described herein, a distal end or portion of a component refers to the end or the portion that is closer to a patient's body during use thereof. On the other hand, a proximal end or portion of the component refers to the end or the portion that is distanced further away from the patient's body.

Base unit 220 further provides a port 223 at a proximal end 225 thereof for one or more supply lines to be routed into an interior chamber of the base unit 220. In certain embodiments, port 223 may be representative of two or more ports. In certain embodiments, port 223 may provide a connection between the base unit 220 and a tube or vacuum line (e.g., line 105 of FIG. 1) of a vacuum generator (e.g., a vacuum generator in surgical console 101) for aspiration. In certain embodiments, port 223 may provide a connection to an optical fiber cable that couples to one or more laser light sources (e.g., in surgical console 101) for providing laser light that is used by vitrector 203 for cutting the vitreous. In certain embodiments, port 223 may provide a connection to pneumatic line that that couples a pneumatic module (e.g., in surgical console 101) that uses compressed gas, such as nitrogen, to power vitrector 203 for cutting the vitreous. Note the vitrector 203 may be powered using other technologies, as one of ordinary skill in the art appreciates. As further described in relation to FIG. 4, vitrector 203 comprises a cutting port 216 at the distal portion of probe 210. In certain embodiments, vitrector 103 is able to cut and aspirate the vitreous through this port 216.

Figure 4:
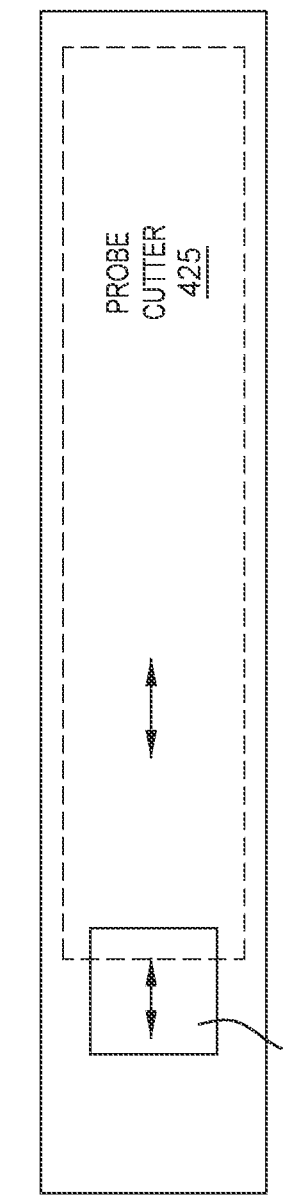
FIG. 4 illustrates an example cutting mechanism of the vitrectomy probe of FIG. 2, in accordance with certain embodiments.

FIG. 4 illustrates an example of a cutting mechanism used in conjunction with vitrector 203 of FIGS. 2 and 3. More specifically, FIG. 4 illustrates the distal end of probe 210 of vitrector 203, the distal end probe 210 housing a probe cutter 425 that acts as a cutting device. Probe cutter 425 reciprocates inside probe 210. In certain embodiments, probe cutter 425 is a hollow tube with a sharpened tip. In certain embodiments, probe cutter 425 comprises a cutter port that is similar to and interacts with cutter port 216 of probe cutter 425 to increase the cutting efficiency and effectiveness. As the probe cutter 425 moves back and forth, the probe cutter 425 alternately opens and closes cutter port 216 with the sharpened tip of probe cutter 425. Each cycle of the probe cutter 425 through the distal end of probe 210 may cut through material such as vitreous in the cutter port 216 as the probe cutter 425 is closing. The surgically cut vitreous is then aspirated through probe 210. In certain embodiments, the surgically cut vitreous is aspirated from the circular area between the outer surface of probe cutter 425 and the inner surface of probe 210. In certain embodiments, the surgically cut vitreous is, in addition or instead, aspirated through probe cutter 425 (e.g., through the hollow compartment thereof).

Note that FIGS. 2-3 illustrate only one example of a vitrector. Also, FIG. 4 illustrates only one example of a cutting mechanism that may be used as part of a vitrector. As described above, laser light or other mechanism may instead be used. Further, tool 103 may be a phacoemulsification probe, such as the one shown in FIG. 5.

Figure 5:
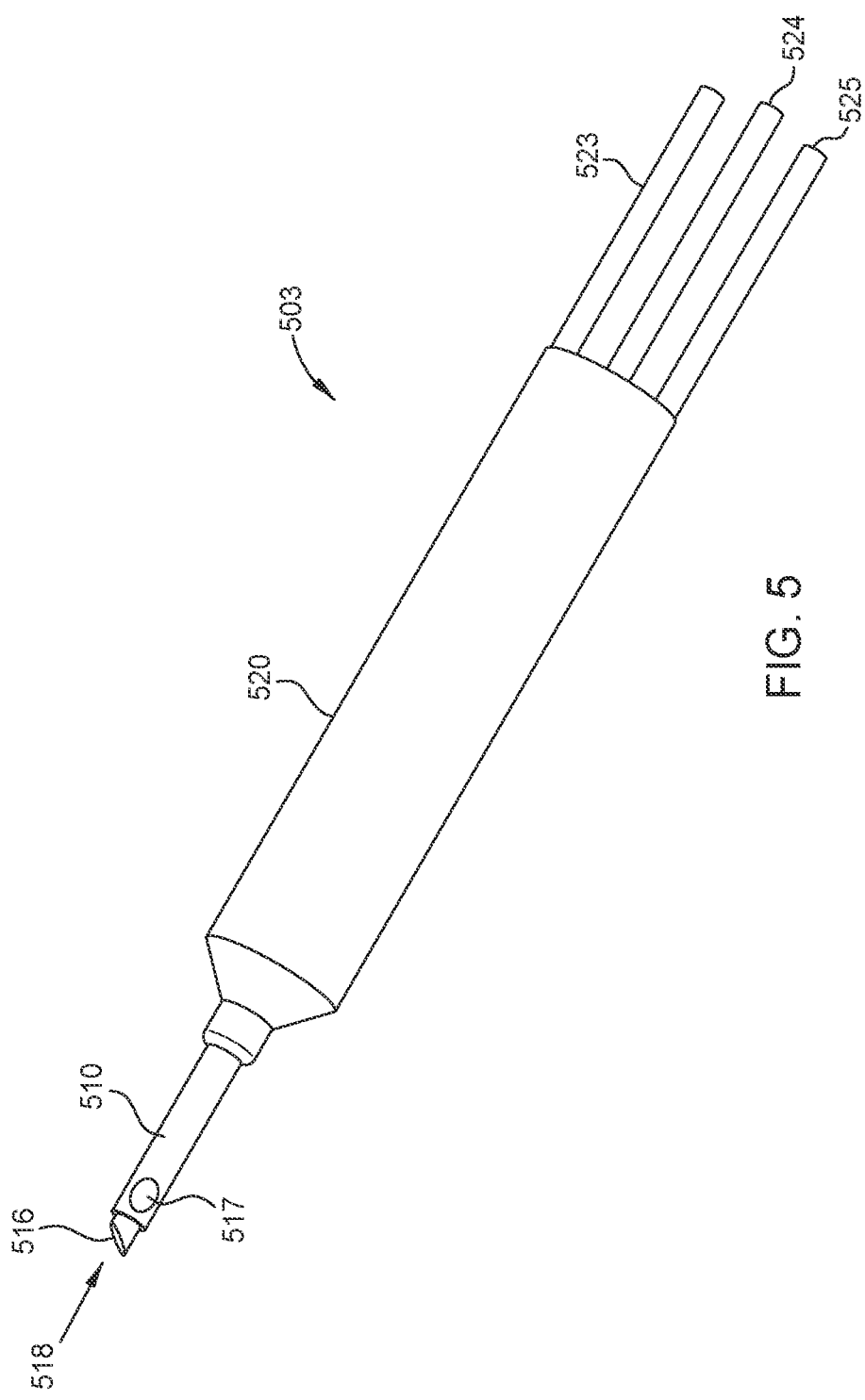
FIG. 5 illustrates an example phacoemulsification probe, in accordance with certain embodiments.

FIG. 5 illustrates an example phacoemulsification probe 503 including a handpiece body 520 and probe 510 that may be inserted into an eye for performing phacoemulsification. A cutting tip 516 extends beyond the distal end of probe 510. Cutting tip 516 is a hollow cylindrical tube or shaft that propagates ultrasound waves provided by an ultrasound power line 524. The ultrasound waves emulsify the lens. Cutting tip 516 also provides an aspiration port 518 through which the emulsified lens is aspirated as a result of the vacuum pressure provided by an aspiration line 523. Probe 510 also has an irrigation port for irrigating the lens during the phacoemulsification process. Note that FIG. 5 illustrates only one example of a phacoemulsification probe. Also, FIG. 5 only illustrates one example of an emulsification mechanism that may be used as part of a phacoemulsification probe.

Figure 6:
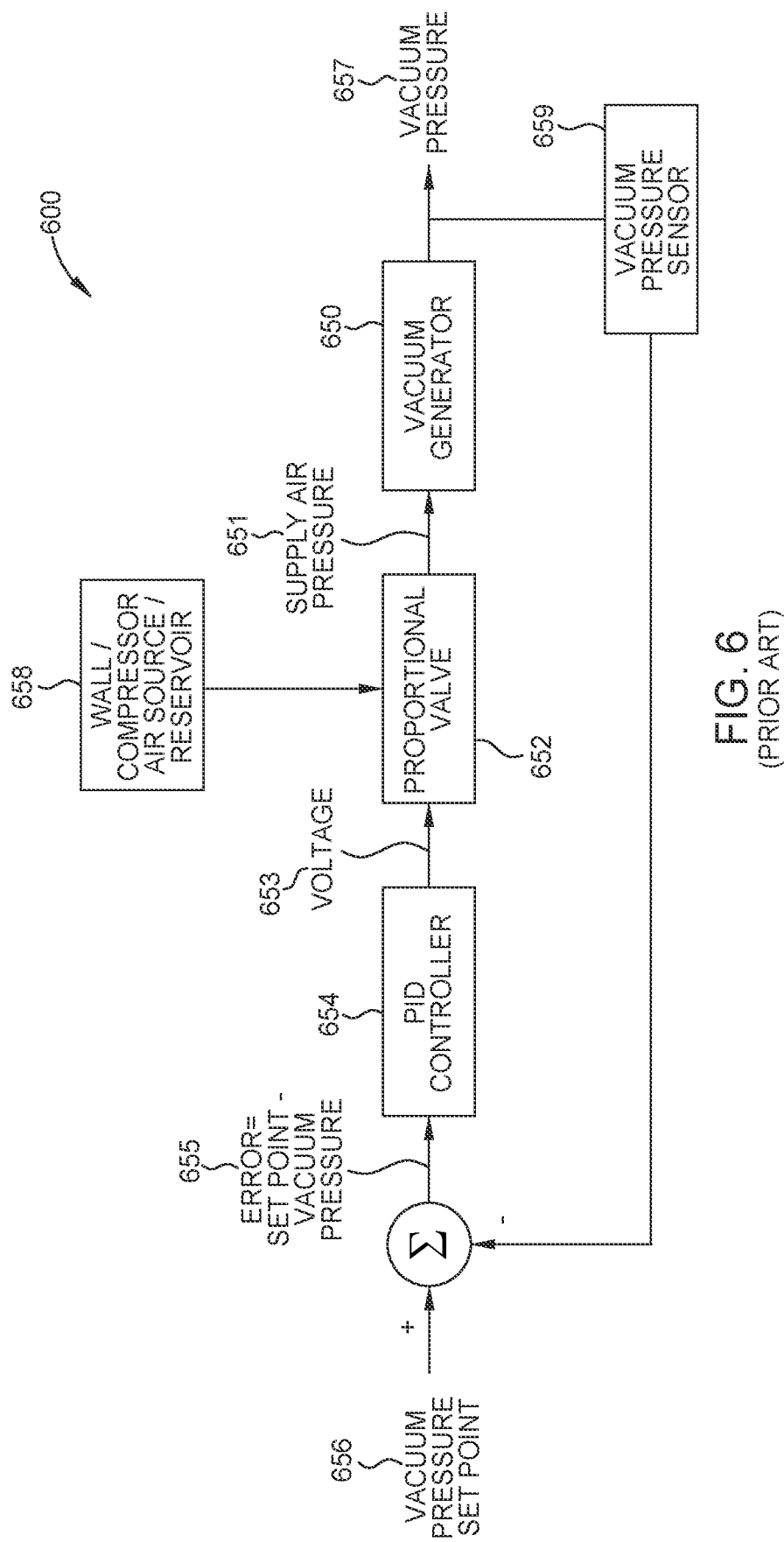
FIG. 6 illustrates a prior art vacuum generation system, in accordance with certain embodiments.

As described above, certain existing vacuum generators, that may be used to enable a tool 103 (e.g., vitrector 203, phacoemulsification probe 503, etc.) to aspirate material from a surgical site (e.g., a patient's eye), operate using compressed air to flow through orifices that generate vacuum pressure. However, a common property of these vacuum generators is that beyond a certain amount of supply air pressure, the vacuum generator becomes less efficient and generates less vacuum pressure as supply air pressure increases. FIG. 6 illustrate examples operations of these vacuum generators.

FIG. 6 illustrates a high-level diagram that illustrates operations of an example prior art vacuum generation system 600. As shown, vacuum generation system 600 comprises a vacuum generator 650, such as a venturi vacuum, that generates vacuum pressure. As described above, vacuum generation system 600 may be positioned in a surgical console (e.g., surgical console 101) that couples to tool 103. As such, the vacuum pressure that is provided by vacuum generation system 600 may be used for the aspiration procedures described above. Vacuum generation system 600 also includes a proportional valve 652. Vacuum generator 650 takes as input supply air, whose pressure (i.e., supply air pressure 651) is set by proportional valve 652, and creates vacuum with a certain vacuum pressure 657. In certain embodiments, vacuum generator 650 is a Venturi vacuum generator that creates vacuum by a pump with supply air running through the pump. One of ordinary skill in the art appreciates the inner-workings of a Venturi vacuum generator, and, therefore, details relating to such inner-workings are not described herein for brevity.

As described above, proportional valve 652 sets the supply air pressure 651 for the supply air that is provided to vacuum generator 650. A proportional valve provides a change in output pressure or flow in the same ratio as the change in the input. For example, if the input doubles then the output will also double. In FIG. 6, proportional valve 625 is operatively coupled to an air compressor or air source reservoir 658. Proportional valve 625 takes as input compressed air and regulates the pressure (by providing less or more air) based on the input voltage 653 that is provided to proportional valve 652. The higher the voltage 653 the higher the supply air pressure 651. Vacuum generation system 600 further comprises a PID controller 654, which is used to control vacuum pressure 657. Generally, a PID controller provides calculations for driving an actuator (e.g., proportional valve 652) based on an amount of error (calculated as the difference between the desired set point and the last sensor reading), integral, and derivative of the error tend.

To illustrate the operations of PID controller 654 with a simple example, PID controller 654 takes as input an error value that corresponds to the difference between the current vacuum pressure and a vacuum pressure set point 656. PID controller 654 then computes both the derivative and the integral of this error value with respect to time. Based on such a computation, PID controller 654 then provides an output (e.g., in the form of a voltage value). The output may be calculated in different ways, as one of ordinary skill in the art appreciates. In one example, the output may be equal to the proportional gain ($K_P$) times the magnitude of the error plus the integral gain ($K_i$) times the integral of the error plus the derivative gain ($K_d$) times the derivative of the error.

Vacuum pressure set point 656 refers to a certain vacuum pressure that may be desired by the user of a corresponding tool 103 (e.g., vitrector 203, phacoemulsification probe 503, etc.). The user may change the vacuum pressure set point 656 by providing input to surgical console 101 through a graphical user-interface displayed on display 109 of surgical console 101, a foot pedal of surgical console 101, or through some other mechanism. The current vacuum pressure refers to the last sensor reading of the vacuum pressure that is provided to PID controller 654 by a vacuum pressure sensor 659. For example, vacuum pressure sensor 659 may periodically or continuously sense the current vacuum pressure.

PID controller 654, therefore, periodically or continuously calculates the amount of voltage 653 that should be provided to proportional valve 652 (e.g., using a driver circuit) to help vacuum generation system 600 ultimately achieve the vacuum pressure set point 656. As described above, the higher the voltage 653 the higher the supply air pressure 651 and, therefore, the higher the vacuum pressure 657. As such, by controlling the voltage 653 based on the error calculated by the PID controller 654, vacuum generation system 600 is able to control the vacuum pressure 657.

However, in vacuum generation system 600, beyond a certain amount of supply air pressure 651, vacuum generator 650 becomes less efficient and generates less vacuum pressure 657 as supply air pressure increases 651.

Figure 7:
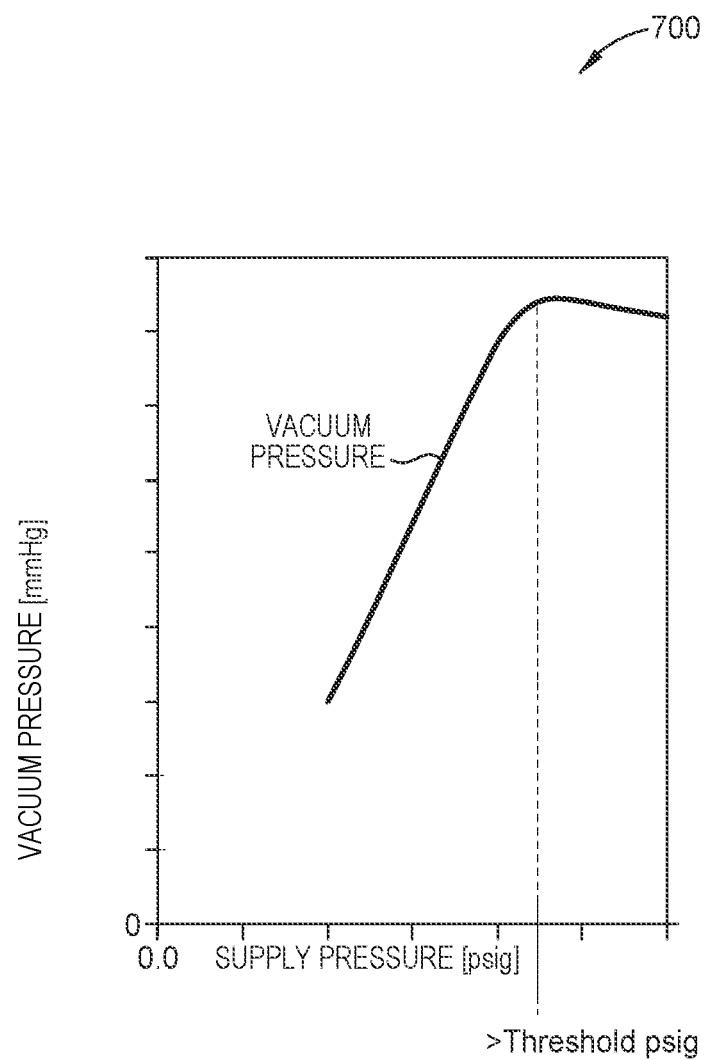
FIG. 7 illustrates a vacuum generation performance graph associated with the prior art vacuum generation system of FIG. 6, in accordance with certain embodiments.

FIG. 7 illustrates a vacuum generation performance graph 700 of a prior art vacuum generation system, such as vacuum generation system 600. As shown in graph 700, the vacuum pressure (measured in mmHg, which refers to a millimeter of mercury) increases as the supply air pressure increases in the range of 0 to a certain threshold (e.g., 60 psig (pounds per square inch gauge)). However, the vacuum pressure begins to decrease as the supply air pressure increases above the threshold. For example, when the supply air pressure reaches around 60 psig and increase, vacuum pressure starts decreasing, thereby causing a standard PID controller (e.g., PID controller 654) to drive to instability. Note that 60 psig is an example and different vacuum generators may have different thresholds.

Using a single PID controller, such as in the manner described in relation to vacuum generation system 600, therefore, causes vacuum generation system 600 to become unstable if the system reaches the decreasing or non-monotonic region (e.g., 60-87 psig). For example, in such situations, PID controller 654 senses that the vacuum pressure 657 is lower than the vacuum pressure set point 656, which causes PID controller 654 to increase voltage 653. The increased voltage opens proportional valve 652 even more, allowing more supply air (i.e., higher supply air pressure 651), which causes vacuum generator 650 to decrease vacuum pressure 657 even more. The additional reduction in vacuum pressure 657 causes PID controller 654 to increase voltage 653 again, and the cycle repeats. In such a situation, vacuum generation system 600 is driven to its limits and becomes unstable. To recover from this instability, vacuum pressure set point 656 must be reduced to be lower than the current vacuum pressure 657, which causes PID controller 654 to decrease voltage 653 until vacuum generation system 600 is back in the monotonic region (e.g., 0-60 psig of supply air pressure). As such, vacuum generation system 600 may experience an initial increase and then a decrease of the vacuum pressure until vacuum pressure set point 656 is reached. As a result, vacuum generation system 600 may experience a sluggish or slow performance in reaching a desired vacuum pressure set point, in the situations described above.

Accordingly, certain embodiments described herein relate to a vacuum generation system with a cascade PID controller, including an outer loop PID controller and an inner loop PID controller. The outer loop PID controller is configured to make calculations based on an error between the current vacuum pressure and the vacuum pressure set point while the inner loop PID controller is configured to make calculations based on an error between the current supply air pressure and a supply air pressure set point.

Figure 8:
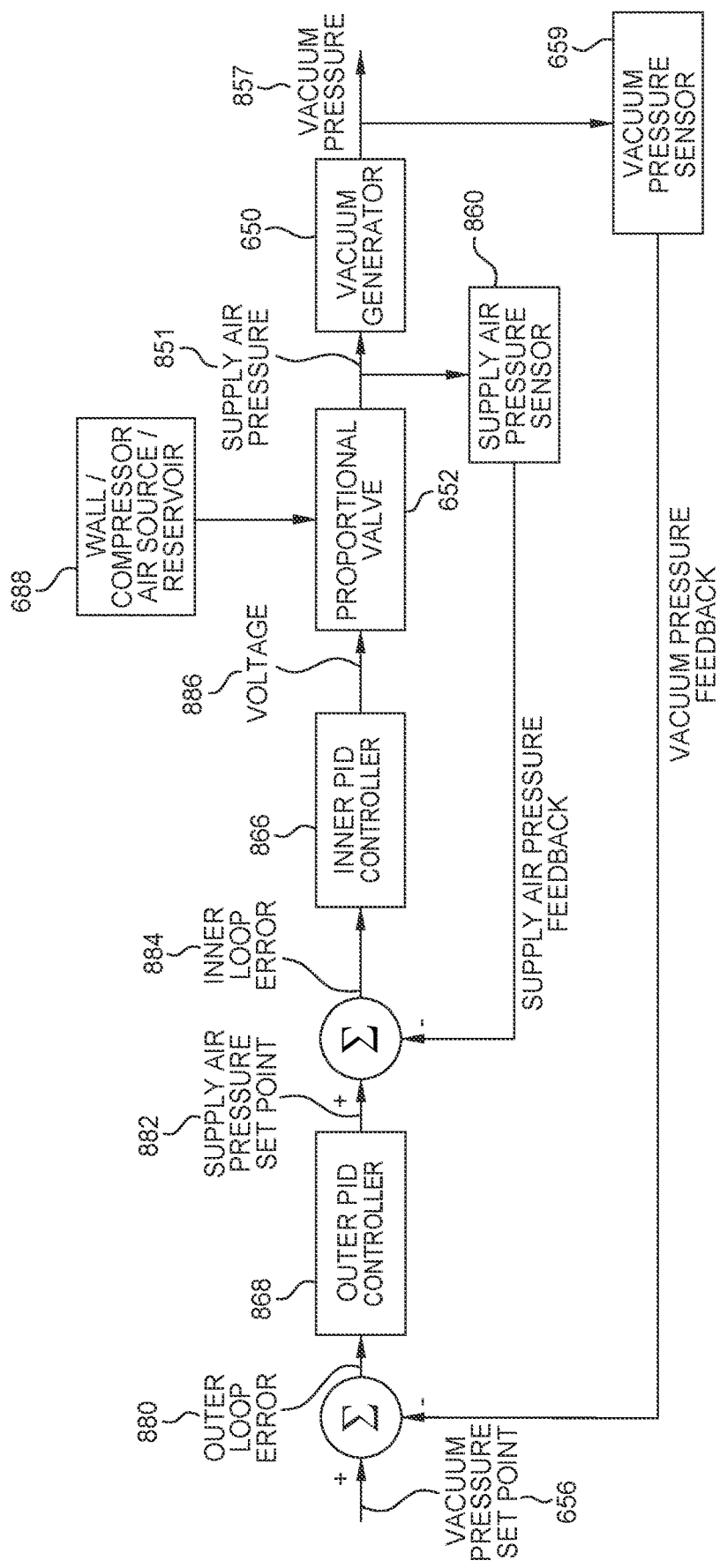
FIG. 8 illustrates an example schematic vacuum generation system with cascade PID controllers, in accordance with certain embodiments.

FIG. 8 illustrates a high-level diagram that illustrates example operations of a vacuum generation system 800, in accordance with certain embodiments. As shown, vacuum generation system 800 includes an outer PID controller 868 that is configured to take as input an outer loop error 880 that corresponds to the difference between the current vacuum pressure 857 (corresponding to the latest sensor reading provided by vacuum pressure sensor 659), and vacuum pressure set point 656. Using outer loop error 880, outer PID controller 868 is then configured to compute both the derivative and the integral of outer loop error 880 with respect to time. Based on such computations, outer PID controller 868 is configured to provide a supply air pressure set point 882 as output. In certain embodiments, outer PID controller 868 may be configured to limit the output (supply air pressure set point 882) to the range of 0-60 psig (corresponding to the monotonic region of vacuum generator 650). For example, outer PID controller 868 may be configured such as to ensure that a supply air pressure set point 882 does not exceed the defined range. As described further below, limiting the range of the supply air pressure helps with ensuring stability of vacuum generation system 800.

Vacuum generation system 800 further comprises an inner PID controller 866 that takes inner loop error 884 as input, where inner loop error 884 corresponds to the difference between the supply air pressure set point 882 (as provided by outer PID controller 868) and the current supply air pressure 851. The current supply air pressure 851 corresponds to the latest sensor reading that is provided by supply air pressure sensor 860.

Using inner loop error 884, inner PID controller 866 is then configured to compute both the derivative and the integral of inner loop error 884 with respect to time. Based on such computations, inner PID controller 866 is configured to determine a voltage value as output. A certain amount of voltage 886, corresponding to the voltage value calculated by inner PID controller 866, is then provided to proportional valve 652. Proportional valve 652 then sets the supply air pressure 851 based on the provided voltage 886. As described previously, vacuum generator 650 takes as input supply air, whose pressure (i.e., supply air pressure 651) is set by a proportional valve 652, and creates vacuum with a current vacuum pressure 857. In certain embodiments, inner PID controller 866 is configured to limit its output to the operating range of proportional valve 652. For example, if proportional valve 652 is a 5 V (Volt) actuator, then inner PID controller 866 is configured to limit its output to a range of 0-5 V.

Using both outer PID controller 868 and inner PID controller 866 allows vacuum generation system 800 to control vacuum pressure 857 by limiting the range of supply air pressure 851 that is provided into the vacuum generator 650, thereby eliminating or reducing the likelihood of vacuum generator 650 operating in its decreasing and non-monotonic range. More specifically, the outer PID loop, involving the outer PID controller 868, uses the vacuum pressure feedback, which includes the current vacuum pressure (primary parameter), and the desired vacuum pressure set point 656 to output a supply air pressure set point 882 (intermediate parameter set point). The inner PID loop, involving the inner PID controller 866, then takes supply air pressure set point 882 and supply air pressure feedback, which includes the current supply air pressure (the intermediate parameter), to calculate a desired output that indicates a voltage value. Voltage 886 is then provided to proportional valve 652 based on the calculated voltage value. As such, by limiting the output (supply air pressure) to a certain range, the output of the outer loop (vacuum pressure) can be controlled.

In other words, using a cascade PID controller (e.g., including outer and inner PID controllers), as described herein, allows vacuum generation system 800 to control the operating range of an intermediate parameter (supply air pressure), based on which vacuum generation system 800 is able to avoid entering the decreasing or non-monotonic region of vacuum generator 650. Preventing vacuum generation system 800 from experiencing accidental suction and entering the decreasing and non-monotonic region of vacuum generator 650 improves performance responsiveness (performance speed) of vacuum generation system 800 because the system does not need to recover from instability.

Note that the cascade PID controller design described herein can be implemented in various other systems that, similar to vacuum generation system 800, work with a primary parameter (vacuum pressure) and an intermediate parameter (supply air pressure), such that the primary parameter (vacuum pressure) is based on an output (voltage value) that is calculated based on the current intermediate parameter (supply air pressure) and an intermediate parameter set point (supply air pressure set point), where the intermediate parameter set point is itself calculated based on the current primary parameter (vacuum pressure) and the primary parameter set point (vacuum pressure set point). In other words, any system that operates with primary and intermediate parameters, such as above, can benefit from the cascade PID controller design described herein.

Also note that the ranges provided here for the inputs, outputs, or set points are exemplary. In other words, these ranges may be tweaked based on manufacturing and/or user preferences as well as the type and characteristics of the components of the system. For example, a vacuum generation system may use a vacuum generator that does not enter its non-monotonic operating range until the supply air pressure reaches 90 psig. In such a case, the range for the supply air pressure set point may be defined as 0-90 psig. In another example, a different type of vacuum generator may enter its non-monotonic operating range when the supply air pressure reaches 40 psig. In such a case, the range for the supply air pressure set point may be defined as 0-40 psig. Other ranges for inputs, outputs, or set points may similarly be changed depending on the factors described above as well as other factors, as one of ordinary skill in the art appreciates.

There are a variety of ways vacuum generation system 800 may be implemented, as one of ordinary skill in the art appreciates. For example, in certain embodiments, all components of the system may be configured to communicate digitally. In such embodiments, the use of digital-to-analog converters (DACs) or analog-to-digital converters (ADCs) may not be necessary. In certain other embodiments, all components of the system may be analog. Similarly, in such embodiments, the use of digital-to-analog converters (DACs) or analog-to-digital converters (ADCs) may not be necessary. In certain other embodiments, some of the components of the system may be analog and some others may be digital. For example, in certain other embodiments, outer PID controller 868 and inner PID controller 866 may correspond to software instructions that can be retrieved from a memory and then executed by a processor. In such embodiments, because any output provided by the processor is digital, digital-to-analog converters (DACs) may be used to allow the processor to communicate with some of the analog components (e.g., a driver circuit, proportional valve 652, etc.) of the system. Similarly, ADCs may be used by certain components, such as supply air pressure sensor 860 and vacuum pressure sensor 659 to communicate with the processor.

Figure 9:
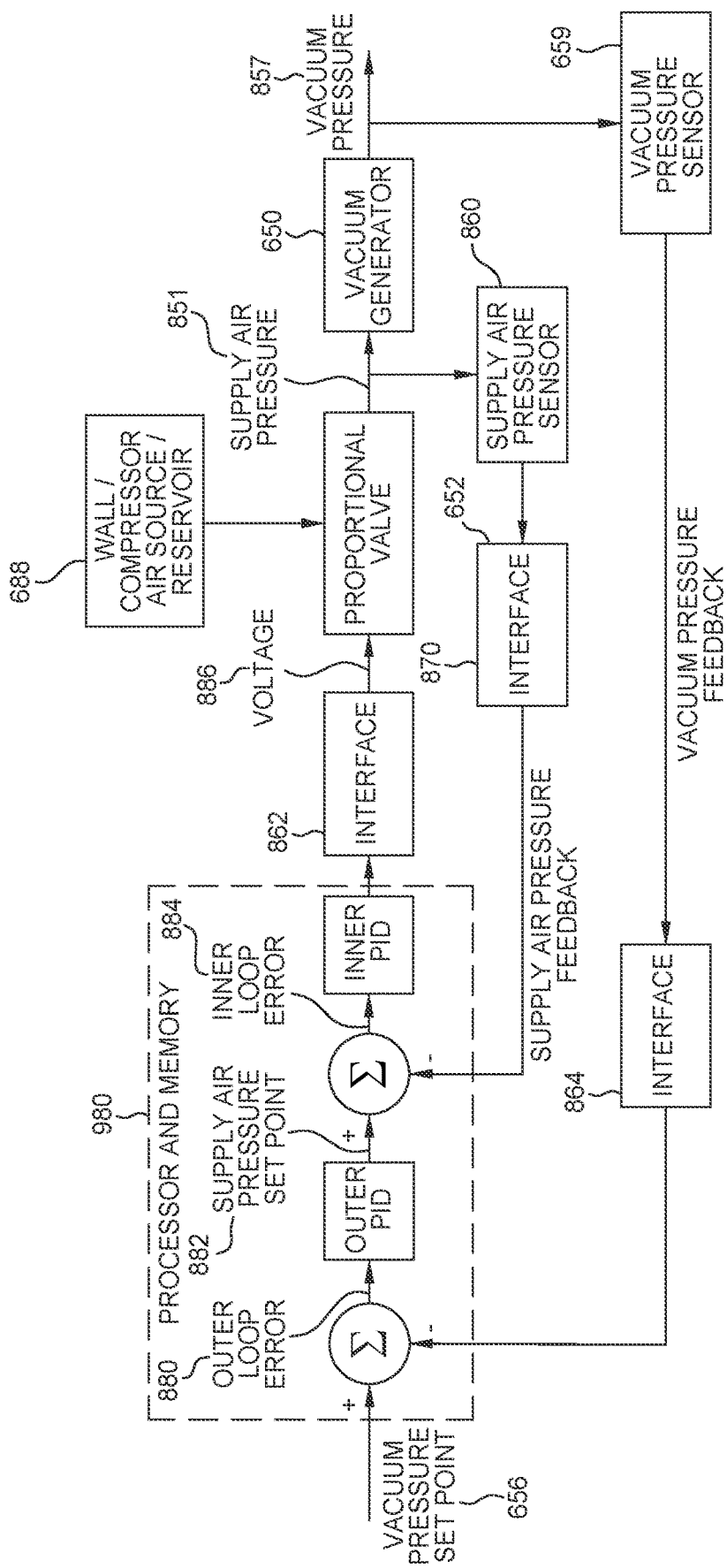
FIG. 9 illustrates an example schematic vacuum generation system with cascade PID controllers, in accordance with certain embodiments.

FIG. 9 illustrates vacuum generation system 900, which corresponds to an example implementation of vacuum generation system 800. Vacuum generation system 900 includes a processor and a memory (collectively referred to as "processor and memory 980") to perform calculations of the outer loop error 880 and the inner loop error 884 as well as the PID calculations of the outer PID controller 868 and the inner PID controller 866. The processor is configured to retrieve and execute programming instructions stored in the memory. The processor may include a single CPU, multiple CPUs, a single CPU having multiple processing cores, and the like. The memory may be one or more of a readily available memory, such as random access memory (RAM), read only memory (ROM), floppy disk, hard disk, solid state, flash memory, magnetic memory, or any other form of digital storage, local or remote. In certain embodiments, the memory includes instructions, which when executed by the processor, performs the calculations of the outer loop error 880 and the inner loop error 884 as well as the PID calculations of the outer PID controller 868 and the inner PID controller 866. In certain embodiments, the processor and memory 980 may be the main processor and memory of surgical console 101, which may implement or include vacuum generation system 900.

As described above, one or more DACs and ADCs may be used for the communication between the processor and other components in the system. For example, the processor may indicate the calculated voltage value to an interface 862, which may include a DAC as well as a driver circuit. When the driver circuit receives an analog signal from the DAC that indicates the calculated voltage value, the driver circuit provides the corresponding amount of voltage to proportional valve 652. The use of a DAC and a driver circuit is merely exemplary. Other types of interfaces may be used instead, as one of ordinary skill in the art appreciates. Further, in certain embodiments, supply air pressure sensor 860 and vacuum pressure sensor 659 are analog components. As such, supply air pressure sensor 860 may use interface 870, which may be an ADC, to communicate with the processor. Similarly, vacuum pressure sensor 659 may use interface 864, which may be an ADC, to communicate with the processor.

Figure 10:
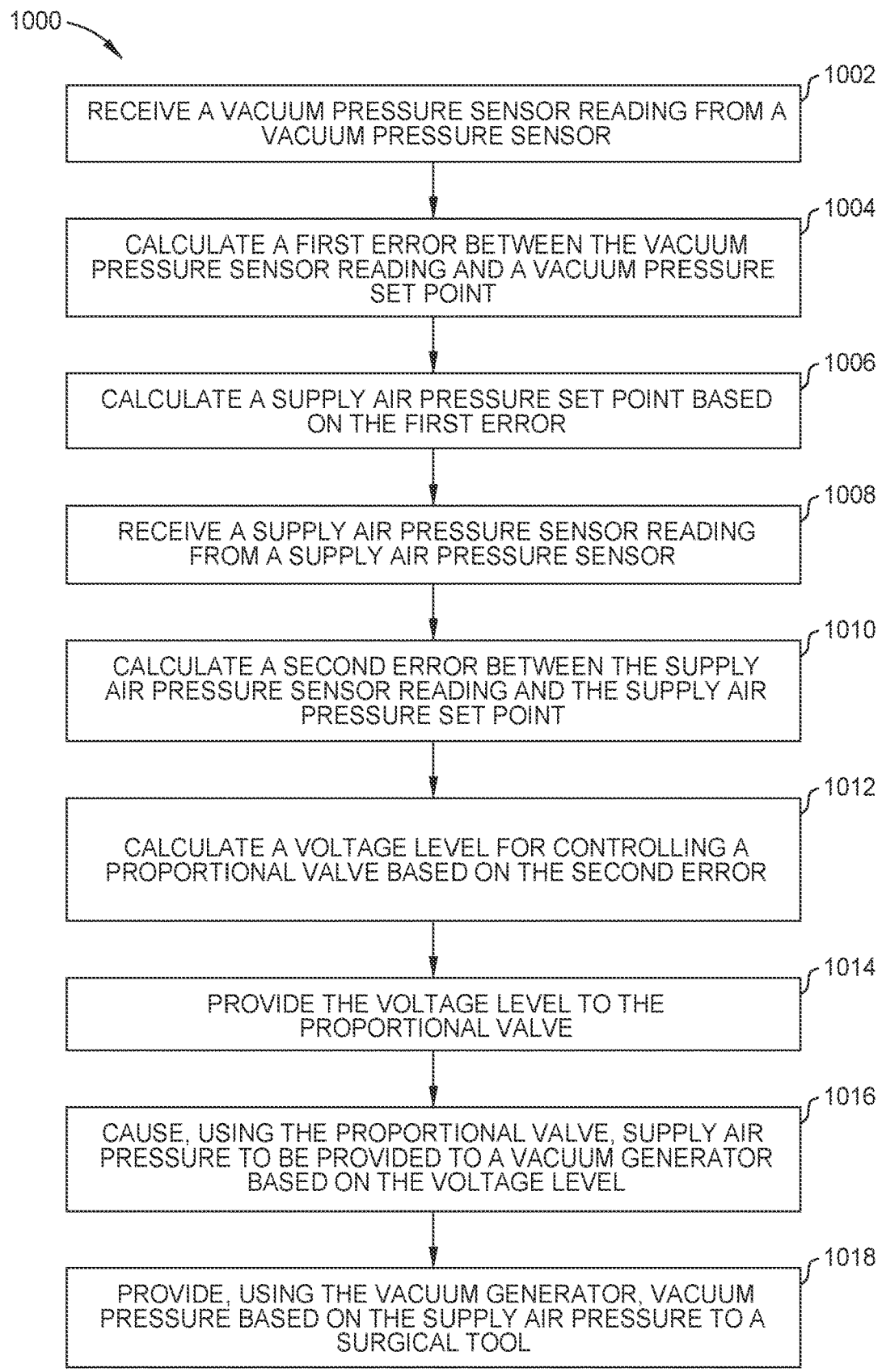
FIG. 10 illustrates example operations of the vacuum generation system of FIG. 8, in accordance with certain embodiments.

FIG. 10 illustrates example operations 1000 of a vacuum generation system, according to some embodiments. In certain embodiments, operations 1000 are performed by the vacuum generation system 800 of FIG. 8. The operations 1000 are described herein with reference to FIG. 8 and its components.

At 1002, a vacuum generation system (e.g., vacuum generation system 800) receives a vacuum pressure sensor reading from a vacuum pressure sensor (e.g., vacuum pressure sensor 659).

At 1004, the vacuum generation system calculates an outer loop error (e.g., outer loop error 880) between the vacuum pressure sensor reading and a vacuum pressure set point (e.g., vacuum pressure set point 656).

At 1006, the vacuum generation system calculates, (e.g., using an outer PID controller (e.g., outer PID controller 868)), a supply air pressure set point (e.g., supply air pressure set point 656) based on the outer loop error.

At 1008, the vacuum generation system receives a supply air pressure sensor reading from a supply air pressure sensor (e.g., supply air pressure sensor 860).

At 1010, the vacuum generation system calculates an inner loop error (e.g., inner loop error 884) between the supply air pressure sensor reading and the supply air pressure set point 882.

At 1012, the vacuum generation system calculates, (e.g., using an inner MD controller (e.g., inner PID controller 866)), a voltage level or value for controlling a proportional valve (e.g., proportional valve 652), the voltage value being based on the inner loop error. The voltage level is associated with an input into the proportional valve.

At 1014, the vacuum generation system provides the voltage level (e.g., voltage with the calculated voltage value) to the proportional valve.

At 1016, the vacuum generation system provides, using the proportional valve, supply air pressure to a vacuum generator (e.g., vacuum generator 650) based on the voltage level.

At 1018, the vacuum generation system provides, using the vacuum generator, vacuum pressure based on the supply air pressure to a surgical tool (e.g., tool 103 of FIG. 1).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Example Embodiments

Embodiment 1: A method of controlling vacuum pressure in a vacuum generation system, the method comprising: receiving a first parameter sensor reading from a first parameter sensor; calculating a first error between the first parameter sensor reading and a first parameter set point; calculating an intermediate parameter set point based on the first error; receiving an intermediate parameter sensor reading from an intermediate parameter sensor; calculating a second error between the intermediate parameter sensor reading and the intermediate parameter set point; calculating a value associated with an input into an actuator based on the second error; providing the input with the calculated value to the actuator; providing, using the actuator, the second parameter to a device based on the input; and providing, using the device, the first parameter based on the second parameter to a tool.

Embodiment 2: A method of controlling vacuum pressure in a vacuum generation system, the method comprising: receiving a first parameter sensor reading from a first parameter sensor; calculating a first error between the first parameter sensor reading and a first parameter set point; calculating, using a first proportional-integral-derivative (PID) controller, an intermediate parameter set point based on the first error; receiving an intermediate parameter sensor reading from an intermediate parameter sensor; calculating a second error between the intermediate parameter sensor reading and the intermediate parameter set point; calculating, a second PID controller, a value associated with an input into an actuator based on the second error; providing the input with the calculated value to the actuator; providing, using the actuator, the second parameter to a device based on the input; and providing, using the device, the first parameter based on the second parameter to a tool.

What is claimed is:

1. A method of controlling vacuum pressure in a vacuum generation system, the method comprising:
receiving a vacuum pressure sensor reading from a vacuum pressure sensor;
calculating a first error between the vacuum pressure sensor reading and a vacuum pressure set point;
calculating a supply air pressure set point based on the first error;
receiving a supply air pressure sensor reading from a supply air pressure sensor;
calculating a second error between the supply air pressure sensor reading and the supply air pressure set point;
calculating a voltage level for controlling a proportional valve based on the second error;
providing the voltage level to the proportional valve;
causing, using the proportional valve, supply air pressure to be provided to a vacuum generator based on the voltage level; and
providing, using the vacuum generator, vacuum pressure based on the supply air pressure to a surgical tool.

2. The method of claim 1, wherein calculating the supply air pressure set point is performed by a first proportional-integral-derivative (PID) controller.

3. The method of claim 2, wherein calculating the voltage level is performed by a second PID controller.

4. The method of claim 1, wherein calculating the supply air pressure set point based on the first error comprises limiting the supply air pressure set point to a range that corresponds to a monotonic operating range of the vacuum generator.

5. The method of claim 1, wherein calculating the supply air pressure set point based on the first error comprises limiting the supply air pressure set point to a range of 0-60 psig (pounds per square inch gauge).

6. The method of claim 1, wherein calculating the voltage level for controlling the proportional valve comprises limiting the voltage level to an operating voltage range of the proportional valve.

7. A vacuum generation system, comprising:
a first proportional-integral-derivative (PID) controller, configured to:
receive a first error between a vacuum pressure sensor reading associated with a vacuum generator and a vacuum pressure set point;
calculate a supply air pressure set point based on the first error;
a second PID controller, configured to:
receive a second error between a supply air pressure sensor reading and the supply air pressure set point;
calculate a voltage level based on the second error;
the proportional valve, configured to:
receive the voltage level;
cause supply air pressure to be provided to a vacuum generator based on the voltage level;
the vacuum generator, configured to:
provide vacuum pressure based on the supply air pressure to a surgical tool.

8. The vacuum generation system of claim 7, further comprising:
a vacuum pressure sensor, configured to provide the vacuum pressure sensor reading; and
a supply air pressure sensor, configured to provide the supply air pressure sensor reading.

9. The vacuum generation system of claim 7, wherein the first PID controller being configured to calculate the supply air pressure set point based on the first error comprises the first PID controller being configured to limit the supply air pressure set point to a range that corresponds to a monotonic operating range of the vacuum generator.

10. The vacuum generation system of claim 7, wherein the first PID controller being configured to calculate the supply air pressure set point based on the first error comprises the first PID controller being configured to limit the supply air pressure set point to a range of 0-60 psig (pounds per square inch gauge).

11. The vacuum generation system of claim 7, wherein the second PID controller being configured to calculate the voltage level for controlling the proportional valve comprises the second PID controller being configured to limit the voltage level to an operating voltage range of the proportional valve.

12. A vacuum generation system, comprising:
a memory comprising executable instructions;
a processor in data communication with memory and configured to execute the instructions, which configured the processor to;
receive a first error between a vacuum pressure sensor reading associated with a vacuum generator and a vacuum pressure set point;
calculate a supply air pressure set point based on the first error;
receive a second error between a supply air pressure sensor reading and the supply air pressure set point;
calculate a voltage level based on the second error;
cause the voltage level to be provided to the proportional valve;
the proportional valve, configured to:
cause supply air pressure to be provided to a vacuum generator based on the voltage level;
the vacuum generator, configured to:
provide vacuum pressure based on the supply air pressure to a surgical tool.

13. The vacuum generation system of claim 12, further comprising:
a vacuum pressure sensor, configured to provide the vacuum pressure sensor reading; and
a supply air pressure sensor, configured to provide the supply air pressure sensor reading.

14. The vacuum generation system of claim 12, wherein calculating the supply air pressure set point based on the first error comprises limiting the supply air pressure set point to a range that corresponds to a monotonic operating range of the vacuum generator.

15. The vacuum generation system of claim 12, wherein calculating the supply air pressure set point based on the first error comprises limiting the supply air pressure set point to a range of 060 psig (pounds per square inch gauge).

* * * * *